United States Patent
Kusanagi et al.

(10) Patent No.: US 7,560,432 B2
(45) Date of Patent: *Jul. 14, 2009

(54) *IN SITU* METHOD FOR TREATMENT AND REPAIR OF MENISCAL INJURIES

(75) Inventors: Akihiko Kusanagi, Brookline, MA (US); Mary Beth Schmidt, Pomfret Center, CT (US); Laurence J. B. Tarrant, Northampton, MA (US)

(73) Assignee: Histogenics Corporation, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/285,928

(22) Filed: Nov. 23, 2005

(65) Prior Publication Data

US 2006/0160734 A1 Jul. 20, 2006

Related U.S. Application Data

(63) Continuation-in-part of application No. 10/998,230, filed on Nov. 26, 2004, now Pat. No. 7,157,428.

(60) Provisional application No. 60/525,247, filed on Nov. 26, 2003.

(51) Int. Cl.
*A61K 38/39* (2006.01)
*C07K 14/78* (2006.01)

(52) U.S. Cl. .................. 514/12; 530/356; 424/9.1

(58) Field of Classification Search .............. None
See application file for complete search history.

(56) References Cited

U.S. PATENT DOCUMENTS

| 5,306,500 | A | 4/1994 | Rhee et al. |
| 7,157,428 | B2 * | 1/2007 | Kusanagi et al. ........... 514/12 |
| 7,217,294 | B2 * | 5/2007 | Kusanagi et al. ........ 623/18.11 |
| 2004/0062753 | A1 * | 4/2004 | Rezania et al. ............ 424/93.7 |
| 2005/0043814 | A1 | 2/2005 | Kusanagi et al. |

FOREIGN PATENT DOCUMENTS

EP 1264607 A1 11/2002

* cited by examiner

*Primary Examiner*—Chih-Min Kam
(74) *Attorney, Agent, or Firm*—Peters Verny, LLP; Hana Verny

(57) ABSTRACT

A method for in situ repair of meniscal injuries comprising induction of meniscal repair and regeneration by introducing an adhesive collagen-polyethylene glycol (PEG) hydrogel to a site of injury alone, supplemented with a synovial tissue or in conjunction with a support matrix.

13 Claims, 6 Drawing Sheets

FIG. 6
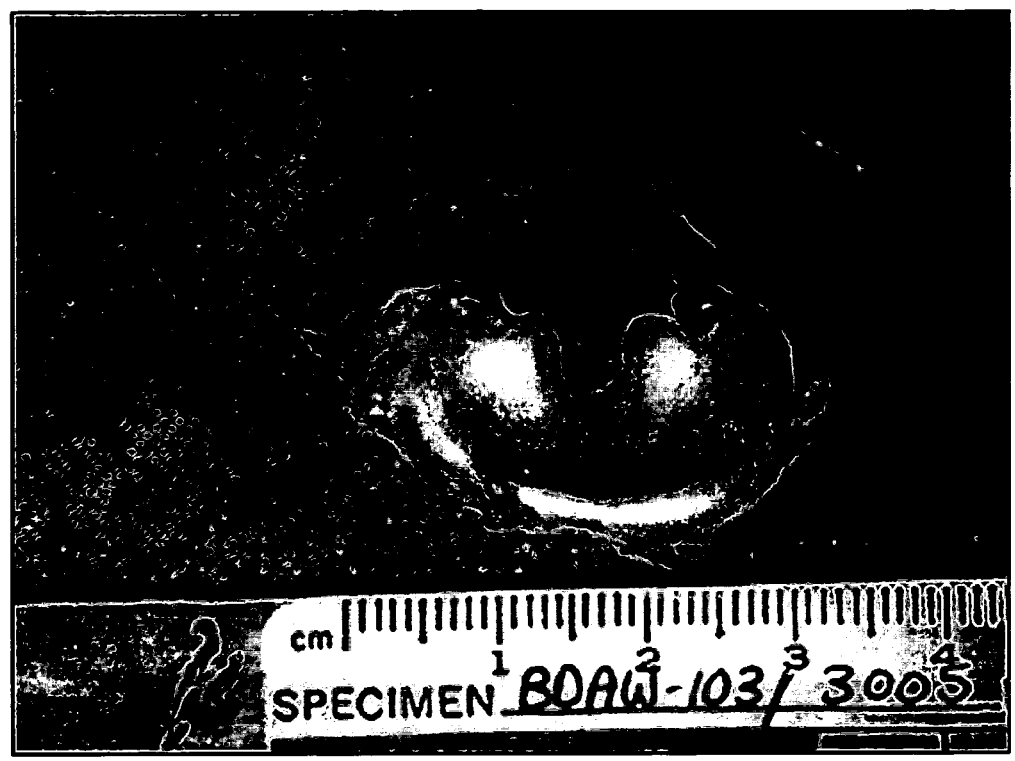
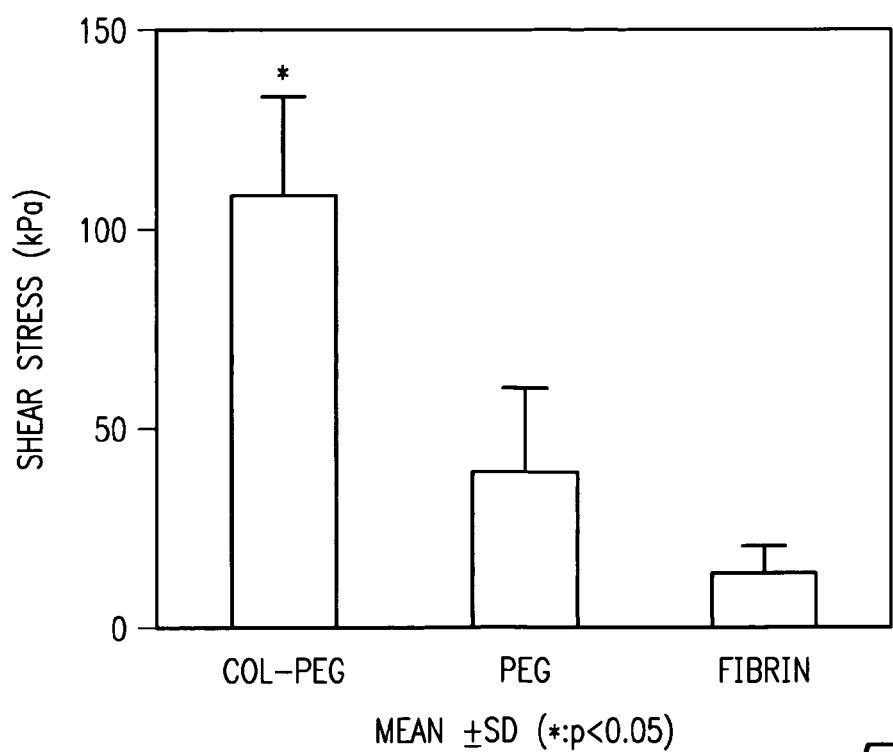
MEAN ±SD (*:p<0.05)
FIG. 8

IN SITU METHOD FOR TREATMENT AND REPAIR OF MENISCAL INJURIES

This application is a Continuation-in-Part application of U.S. patent application Ser. No. 10/998,230, filed on Nov. 26, 2004, now U.S. Pat. No. 7,157,428, which claims benefit of Provisional Application Ser. No. 60/525,247, filed Nov. 26, 2003.

BACKGROUND OF THE INVENTION

1. Field of the Invention

This invention concerns an in situ method for repair of meniscal injuries. In particular, the invention concerns a minimally invasive method for repair of meniscal injuries comprising induction of meniscal regeneration in situ by introducing an adhesive collagen-polyethylene glycol (PEG) hydrogel to a site of injury. The collagen-PEG hydrogels strongly bind the torn region of the meniscus for a period of time needed for healing and promote cell migration and extracellular matrix formation in the torn zone.

2. Background and Related Disclosures

Repair of meniscal injuries is one of the most common operative procedures utilized in orthopedics surgery today (Koski J A, Ibarra C, Rodeo S A, Warren R F: Meniscal Injury and Repair-Clinical Status. *Tissue Engr. Orthop. Surg.*, 31(3):419-435 (2000)).

Meniscal tears are common in young individuals, usually as a result of sports-related activities, as well as in older population suffering from degenerative joint diseases. The meniscus plays an important role in load transmission, shock absorption and knee joint stability. Injuries to the meniscus cause pain, disability and damage to the articular cartilage on the femoral and tibial surfaces, leading to development of degenerative changes and osteoarthritis.

Early treatments for meniscal injuries typically consists of partial or total meniscectomy. This approach frequently results in accelerated cartilage degeneration due to decreased joint contact area and the resultant rise in contact stress. Removal of only 15-34% of the meniscus can produce a 350% increase in contact stress (Seedhon B, Hargreaves, D: Transmission of the load in the knee joint with special references to the role of the menisci: II. Experimental results, discussion, and conclusions. *Engineering in Med.*, 8:220 (1979)). Therefore, preservation of meniscal tissue and successful lesion repair are the goals of most current treatment methods for meniscal injury.

Currently, a meniscal transplantation is one of the available treatment options for patients whose injury, such as a meniscal tear, is severe and complex. Fresh-frozen allograft menisci have been shown to successfully attach and heal to the recipient periphery in experimental models. Studies have also shown evidence of repopulation of the allograft with host-derived cells. The clinical studies show that 71% of meniscal transplants result in complete healing at 8 months post operation. Despite these positive results, issues with availability of allograft tissue, tissue rejection, disease transmission and a lack of long-term data have limited the use of this approach.

The ability of a meniscal lesion to heal, either spontaneously or after surgical repair, is influenced by the proximity of the tear to the limited vascular supply, the size and complexity of the tear, and the presence of concurrent ligamentous instability. Lesions located in the peripheral 10-25% of the meniscus, in so called red zone where vascularity is greatest, have the greatest chance for successful repair. Lesions in the remaining avascular region of the meniscus, so called white zone, have shown only limited capacity, if at all, for repair and healing.

Recognizing the importance of the formation of a fibrin clot to the healing process, several researchers have used an autologous clot to enhance repair of avascular meniscal lesions. Using a canine model with stable 2 mm diameter defects filled with a fresh blood clot, fibrous reparative tissue was observed to fill in the defect site. The clot was thought to provide a scaffold for cell migration and proliferation, as well as chemotactic and mitogenic stimuli such as platelet-derived growth factor and fibronectin. However, in these studies, the histological appearance of the reparative tissue was notably significantly different from normal meniscus. Furthermore, cells migrating into the clot did not appear to synthesize a significant amount of extracellular matrix (*Amer. J. Sports Med.*, 17:393-400 (1989). Consequently, the reported clinical results performed with autologous clots do not have a very positive outcome.

Moving toward a regenerative approach, more recent studies have been directed at developing a resorbable porous collagen scaffold to replace the injured portion of the meniscus when repair is not possible. These scaffolds provide a substrate for migration and repopulation by native cells. See, for example, U.S. application Ser. Nos. 10/626,459, 10/104,677, 10/625,822, 10/625,245 and 10/882,581, by inventors, all hereby incorporated by reference.

Using a canine partial meniscectomy model and an appropriately shaped collagen implant, Stone and co-workers demonstrated that 63% of the implants showed evidence of substantial meniscal regeneration at 12 months (Stone K R, Rodkey W G, Weber R J, Meniscal regeneration with copolymeric collagen scaffolds: In vitro and in vivo studies evaluated clinically, histologically, and biochemically *Am. J. Sports Med.*, 20:104-111 (1992)). In these studies, histologically, the repair tissue seemed similar to normal canine meniscus. The limited clinical results for this approach indicated that regeneration of some meniscus-like tissue could be possible for patients with severe meniscal injuries who would have otherwise have to undergo partial or total meniscectomies.

The studies, described in the above cited patent applications, have shown that through the use of a fibrin clot or other appropriate scaffold material, replacement fibrocartilage can form through cellular integration, proliferation and tissue ingrowth. The regenerative treatment approach provides an appropriate follow-up to meniscectomy, potentially preventing cartilage degradation while restoring the function of the joint. Many meniscal tears in the avascular region are initially small and cause minor discomfort to the patient and, consequently, a significant number of the meniscal tears are left untreated due to the lack of fast, reliable arthroscopic repair techniques which would preserve the functional integrity of the meniscus. Over time, the size of these meniscal tears grows and cause significant cartilage damage, as well as pain and loss of joint mobility.

To overcome the above stated problems, the current invention provides a minimally invasive method for repair of meniscal tear in situ utilizing an arthroscopic procedure to introduce at the site of the meniscal injury an adhesive collagen-PEG hydrogel, preferably supplemented with a source of intra-articular fibroblastic cells or with a support matrix which guides repair of the meniscal tear. Thus, the current invention provides an alternative conservative treatment to a partial meniscectomy.

All patents, patent applications and publication cited herein are hereby incorporated by reference.

SUMMARY OF THE INVENTION

One aspect of this invention concerns a method for minimally invasive repair of meniscal injuries, lesions and tears in situ.

Another aspect of this invention concerns a method for repair of meniscal injuries in situ using an arthroscopic procedure to introduce an adhesive collagen-PEG hydrogel alone or in admixture with a source of intra-articular fibroblastic cells or with a support matrix that promotes a repair of the meniscal injury, lesion or tear.

Still another aspect of this invention concerns a method for use of collagen-PEG hydrogels having strong adhesive properties as a preferred means for repair and regeneration of the meniscus and meniscal tissue in situ.

Still yet another aspect of this invention concerns a method for restoration of the fibrillar network in the injured meniscal tissue wherein such restoration is achieved with an adhesive collagen-PEG hydrogel enhanced by addition of collagen microfibrils prior to hydrogel polymerization.

Yet another aspect of this invention is a method for controlling a rate of polymerization of collagen-PEG hydrogel wherein the rate of polymerization of the hydrogel is controlled by changing pH of the collagen-PEG hydrogel.

Another aspect of this invention concerns a method for repair of the meniscal tissue in situ utilizing the collagen microfibrils in conjunction with the collagen-PEG hydrogel wherein said hydrogel promotes cross-linking of the collagen microfibrils with the broken ends of fibrillar collagen network of the meniscus and wherein the collagen microfibrils in turn enhance the adhesive function of the collagen-PEG hydrogel by their chemical bonding to said hydrogel.

Still another aspect of this invention concerns a method for the restoration of meniscal tissue in situ and for healing large menisacal tears, wherein said restoration and healing is enhanced by addition of a support matrix, with or without collagen-PEG hydrogel or any other hydrogel present in its interior, wherein said support matrix is affixed to the lesion or tear with an adhesive collagen-PEG hydrogel resulting in proliferation of collagen microfibrils throughout the support matrix and in production and in accumulation of Type I collagen and S-GAG in levels corresponding to levels of these compounds observed in healthy meniscal tissue.

Still another aspect of this invention concerns a method for repair of a meniscal tissue in situ by supplementing the collagen-PEG hydrogel with patient's own pleuropotent cells that promote differentiation of meniscal cells in situ, said method comprising an optional step wherein the surgeon, during the arthroscopic surgery, optionally removes a patient's synovial tissue and/or other source of fibroblasts, prepares a suspension therefrom and mix said suspension with the collagen-PEG hydrogel before administration of said hydrogel comprising mixture into a meniscal lesion or meniscal tear.

Another aspect of this invention concerns a method for repair of a meniscal tissue by utilizing a clot from the patient's own blood mixed with the collagen-PEG hydrogel wherein said clot provides autologous growth factors for the stimulation of extracellular matrix production.

Still yet another aspect of this invention concerns a method for repair of meniscal lesions or tears by mixing the collagen-PEG hydrogel with a suspension of the synovial tissue, fibroblasts and autologous growth factors obtained from the patient's blood cloth.

BRIEF DESCRIPTION OF THE DRAWINGS

FIG. 6 shows a Sinclair swine medial meniscus.

FIG. 7 is a schematic illustration of an apparatus used for testing the adhesive strength of three adhesives.

FIG. 8 is a graph showing results of a comparative lap shear test comparing the commercially available fibrin sealant and PEG sealant with the collagen-PEG hydrogel adhesive used in the current method.

DEFINITIONS

Figure 1:
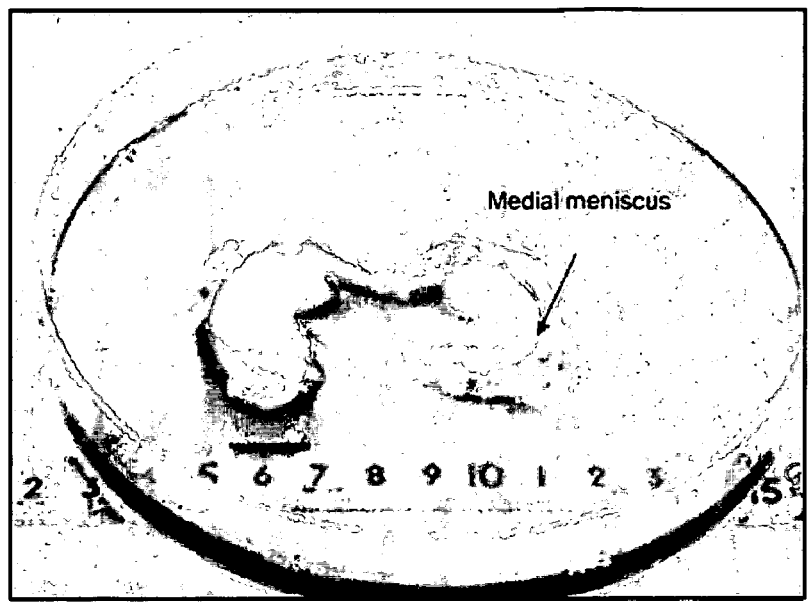
FIG. 1 is a photograph showing a porcine meniscus in culture.

As used herein:

"Collagen-PEG hydrogel", "adhesive collagen-PEG hydrogel" or "hydrogel" means any compound falling within the scope of this definition containing collagen and a hydrogel polymer such as polyethylene glycol (PEG) or derivatized polyethylene glycol, such as, for example, 4-armed polyethylene glycols derivatized with succinimidyl ester and thiol, plus methylated collagen (U.S. Pat. No. 6,312,725 B1, Nov. 6, 2001) or a protein, such as albumin, which is preferably cross-linked with a collagen compound. The collagen-PEG hydrogel of the invention typically gels and/or bonds rapidly upon contact with tissue, particularly with tissue containing collagen.

"Support matrix" means biologically acceptable and biodegradable material suitable for introduction into a meniscal tear or lesion that provides a structural support for growth and three-dimensional propagation of cells. The support matrix is prepared from such materials as Type I collagen, Type II collagen, Type IV collagen, gelatin, agarose, cell-contracted collagen containing proteoglycans, glycosaminoglycans or glycoproteins, fibronectin, laminin, bioactive peptide growth factors, cytokines, elastin, fibrin, synthetic polymeric fibers made of poly-acids such as polylactic, polyglycolic or polyamino acids, polycaprolactones, polyamino acids, polypeptide gel, copolymers thereof and combinations thereof. The gel solution matrix may be a polymeric thermo-reversible gelling hydrogel. The support matrix is preferably biocompatible, biodegradable, hydrophilic, non-reactive, has a neutral charge and be able to have or has a defined structure.

DETAILED DESCRIPTION OF THE INVENTION

The current invention is based on findings that when a meniscal lesion, tear or another injury is treated with an adhesive composition comprising collagen-PEG hydrogel alone or in combination with other regeneration promoting components, agents, additives or accelerants, the meniscal tear may be advantageously healed without major invasive surgical procedure.

This invention, therefore, relates to an in situ method for repair of meniscal lesions, tears and injuries. The invention utilizes approach of a minimally invasive procedure comprising induction of meniscal regeneration by introducing in situ, that is directly to a site of injury, a strongly adhesive collagen-polyethylene glycol (PEG) hydrogel having improved adhesive properties when compared to previously used and commercially available tissue sealants and adhesives. The collagen-PEG hydrogels of the invention strongly bind the torn region of the meniscus for a period of time long enough needed for healing. When supplemented with other agents, additives or accelerants, such as growth hormones, autologous blot clots, collagen microfibrils, etc., such supplemented hydrogels also promote cell migration and extracellular matrix formation in the torn zone. On the other hand, some of these agents, accelerants and additives also enhance the adhesivity of the collagen-PEG hydrogels.

More specifically, the invention concerns identification of adhesive collagen-PEG hydrogel mixtures suitable for treatment of meniscal lesions, tears and injuries in situ as well as identification of additional components aiding in such repair of the meniscus and in restoration of the meniscal functionality.

I. Meniscus

The meniscus is a dimorphic tissue. It consist of two distinctly different tissues, namely so called red zone and so called white zone tissue.

The red zone, located at the meniscal periphery closest to a vascular blood supply, contains primarily cells that are morphologically fibroblastic. Additionally, the red zone contains much lesser amount of an extracellular matrix mass than the white zone. Due to the proximity of the blood supply, lesions, tears and injuries in the red zone of the meniscus heal much more rapidly than those occurring in the white zone. Debridement and suturing of the red zone lesions or tears can usually fully restore meniscal function to the red zone, including the restoration of the red zone collagen fibrillar network.

The injuries in the white zone of the meniscus, on the other hand, are currently almost completely untreatable. The white zone itself has no blood supply and is not even located in the proximity of the blood supply. The white zone contains cells that look like chondrocytes typically observed in the articular cartilage, however, the ratio of the extracellular matrix to cells in the white zone is 10× that of the extracellular matrix found in the articular cartilage. It is well known that the articular cartilage also does not have any blood supply and that the injuries in the articular cartilage are very difficult to treat and if they heal at all the ensuing cartilage is an inferior cartilage, called fibrocartilage, rather than a healthy hyaline cartilage. In this regard the white zone of the meniscus resembles the articular cartilage.

II. Meniscal Injuries and Treatment Thereof

Meniscal injuries, particularly those in the white zone, seriously impair lifestyle of a patient. They can result in altered knee joint function, pain and permanent damage to the adjacent articular cartilage. Due to the avascular nature of the inner white zone region of the meniscus, as described above, a significant number of meniscal lesions or tears do not heal spontaneously or even following the surgery. Left untreated, these lesions and tears can propagate into larger defects that exacerbate cartilage damage and the knee function.

Currently and typically, to treat the injured meniscus, a partial or total meniscectomy is performed. The meniscus removal, however, reduces the stability of the joint and exposes the articular cartilage surfaces to higher contact stresses. Consequently, the aim of the studies leading to this invention was to develop an unique, minimally invasive approach for in situ treatment, said approach comprising induction of regeneration of the meniscal tissue by introducing to the site of the injury the highly adhesive collagen-PEG hydrogel alone or in combination with another agent, accelerant or additive. Such highly adhesive hydrogel fills the gap of the meniscal lesion or tear and holds it together thereby preventing further damage to the meniscus and adjacent articular cartilage. It also provides a means for a rapid repair of meniscal tears and minimizes the degeneration of the articular surfaces of the knee.

A method according to the invention aids such regeneration process by inducing and supporting restoration of the fibrillar network in the red zone, however, the method of the invention is especially useful for the treatment of injuries in the avascular white zone, where meniscal lesions or tears normally do not heal and if they do heal, the fibrillar collagen network that provides the protective resistance to the tear or lesion that exemplifies the ruggedness and functionality of the meniscus is normally not restored. White zone lesions and tears thus require more than close approximation of the lesion surfaces by suturing in order to heal.

It has now been discovered that both the red but particularly the white zone meniscal lesions and tears may be repaired by introducing to a site of the meniscal injury a highly adhesive material comprising collagen and PEG polymer hydrogel complex. The regeneration process and healing of the lesions and tears in the red and white zone may be further augmented by addition of other components which will accelerate or aid this process.

III. Collagen Polyethylene Glycol Hydrogel Complex

A highly adhesive collagen-PEG hydrogel complex according to the invention comprises a mixture of at least collagen or derivatized collagen and polyethylene glycol or derivatized polyethylene glycol. Other components, such as fibroblasts, synovial tissue, blood cloth or healing accelerators may be added to the complex. Additionally, another type of hydrogel, namely a structural hydrogel, typically forming a support matrix, for example collagen honeycomb, collagen sponge or collagen scaffold, may be used in combination with the highly adhesive collagen-PEG hydrogels.

The highly adhesive collagen-PEG hydrogel such as, for example methylated collagen-PEG hydrogel, when deposited into the meniscal injury, lesion or tear fills the tear or lesion, binds to the meniscal tissue and holds the torn region of the meniscal tissue together during the period of healing. Additionally, it also permits or induces cell migration and extracellular matrix formation in the torn zone.

With respect to a long-term binding, collagen-PEG hydrogel complex, particularly such where the collagen is methylated collagen, has much stronger adhesive properties than PEG, collagen or fibrin-based adhesives, and it is far more biocompatible than adhesives comprising epoxies or gluteraldehyde cross-linked materials and the like.

A. Comparative Evaluation of the Collagen-PEG Hydrogel

To evaluate mechanical adhesive property of the collagen-PEG hydrogel, said hydrogel was compared to the two commercially available tissue adhesives, namley TISSEAL® (fibrin sealant) and COSEAL® (PEG sealant).

Figure 7A:
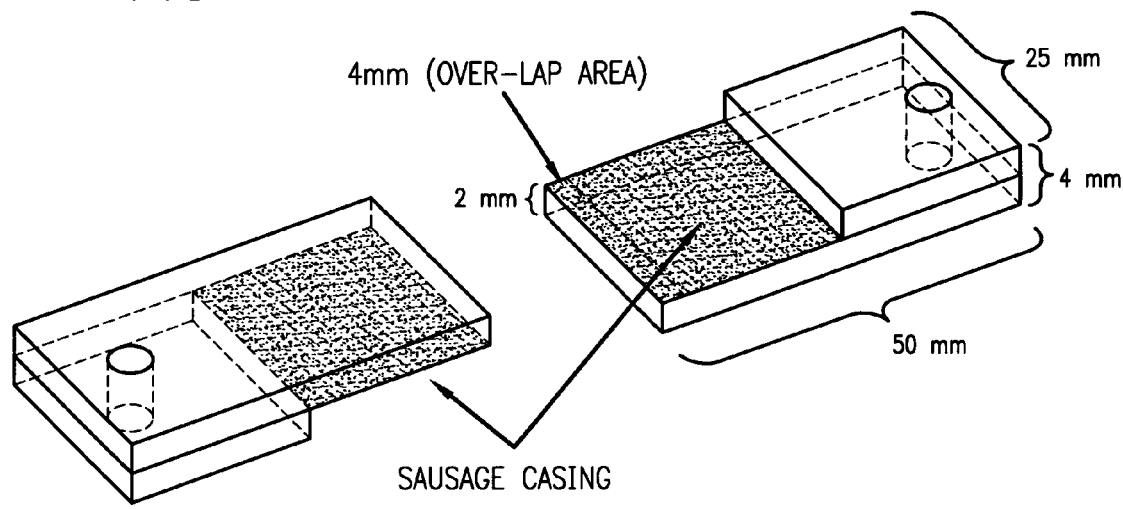
FIG. 7A shows two piece apparatus with over-lap area before the adhesive is applied.
Figure 7B:
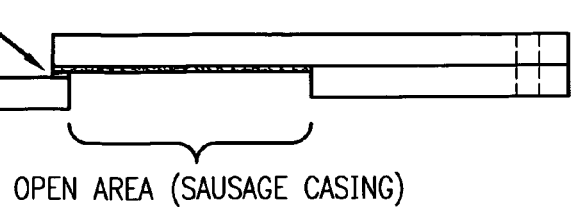
FIG. 7B shows an assembled apparatus wherein the adhesive is applied between two overlapping regions and mechanical properties of collagen-PEG hydrogel vis-a-vis a fibrin sealant and PEG sealant are evaluated.

A lap shear test procedure is described in Example 1. The apparatus used for lap shear determination is seen in FIGS. 7A and 7B. Results of the test are shown in FIG. 8.

As seen in FIG. 8, lap shear strength of the collagen-PEG hydrogel was statically stronger than that of PEG sealant and fibrin sealant ($p<0.05$). Collagen-PEG was significantly greater 9-fold ($P<0.05$) than fibrin sealant, and also significantly greater 3-fold ($P<0.05$) than PEG sealant.

The results of lap shear testing clearly show that the adhesiveness of the collagen-PEG hydrogel is significantly stronger than current commercially available surgical tissue adhesives such as fibrin or PEG alone. These studies also demonstrated that the collagen-PEG hydrogel is advantageous for and supports a cell migration, while the fibrin sealant has poor capacity for cell migration. This finding demonstrates that the use of the collagen-PEG hydrogel is beneficial for repair of the injured tissue which requires very strong tissue adhesion as well as cell migration.

Collagen-PEG hydrogels are complex mixtures containing collagen, collagen compounds or derivatized collagen, such as alkylated, for example methylated collagen, and a hydrogel polymer such as, polyethylene glycol or derivatized polyethylene glycol. These collagen-PEG hydrogels are biologically acceptable and fully biodegradable. In the body, they biodegrade slowly and safely and can thus be left at the site of injury for weeks or months without any detrimental consequences and without need for removal. With respect to inducing cell migration and extracellular matrix formation, collagen-PEG hydrogels contain a network of Type I collagen which provides suitable environment for cell migration from surrounding native meniscal cells.

B. Adhesive Collagen-PEG Hydrogels

The adhesive collagen-PEG hydrogels are biologically acceptable rapidly gelling synthetic compounds complexes having adhesive and/or gluing properties. Most representative of such complexes are complexes comprising a polyethylene glycol (PEG) that is nonderivatized or derivatized, cross-linked with a collagen compound, typically alkylated collagen. Examples of suitable hydrogels are PEG hydrogels derivatized with tetra-hydrosuccinimidyl or tetra-thiol, or a combination thereof, commercially available from Cohesion Technologies, Palo Alto, Calif. under the trade name COSEAL™, described in *J. Biomed. Mater. Res. Appl. Biomater.*, 58:545-555 (2001), or two-part polymer compositions that rapidly form a matrix where at least one of the compounds is polymeric, such as, for example, polyamino acid, polysaccharide, polyalkylene oxide or polyethylene glycol and the second compound is collagen or collagen derivative and wherein two parts are linked through a covalent bond, as described in U.S. Pat. No. 6,312,725B1, herein incorporated by reference. The most preferred is a cross-linked PEG with alkylated collagen, such as a cross-linked polyethylene glycol hydrogel with methylated collagen. The synthetic compound may also be a polyethylene glycol derivatized with, for example, a protein, such as albumin. The hydrogel of the invention typically gels and/or bonds rapidly and strongly upon contact with meniscal tissue.

Collagen-PEG hydrogels are thus complex mixtures containing collagen, collagen compounds or derivatized collagen and a polyethylene glycol hydrogel polymer. PEG may be 4-armed polyethylene glycols derivatized with succinimidyl ester and thiol, described in the U.S. Pat. No. 6,312,725 B1, issued Nov. 6, 2001, hereby incorporated by reference.

The invention is intended to include the use of all collagen-PEG hydrogels having strong adhesive properties.

C. Other Agents, Additives and Accelerants

In addition, the ability of the invention to restore the fibrillar network of the meniscal tissue can be enhanced by mixing the collagen PEG hydrogel with other agents, additives and accelerants whether of the autologous or non-autologous, biological or synthetic origin. For example, autologous collagen microfibrils comprising type I collagen can be added to the collagen-PEG hydrogel complex prior to its polymerization.

The collagen microfibrils can be created by a variety of methods known in the art, such as for example, electrospinning techniques. When microfibrils are added to the collagen-PEG hydrogel complex, the complex promotes crosslinking of the collagen microfibrils with the broken ends of fibrillar collagen network of the meniscus. This process further enhances therapeutic function of the collagen-PEG hydrogel and results in faster repair of the meniscal injury and restoration of the meniscus to its full functionality. The addition of collagen microfibrils, additionally, enhances the adhesive function of the collagen-PEG hydrogel by chemical bonding to it.

Moreover, to stimulate rapid healing, endogenously present compounds, such as all suitable accelerants, growth factors, PDFG and typical blood components can be added to the adhesive collagen-PEG hydrogel.

Since the meniscus has relatively low cellularity and a highly organized structure, additional cells and/or an appropriate support matrix may be advantageously added to achieve faster healing and effective remodeling of an injury site.

Either the collagen-PEG hydrogel alone or the collagen-PEG hydrogel complex augmented with other agents, additives or accelerants is easily applied arthroscopically after injury occurs. No meniscal tissue need to be removed, preserving the limited cell population within the tissue and protecting the articular cartilage surfaces. The strong chemical bonds created by the collagen-PEG hydrogel in both approaches allow faster patient rehabilitation and an early return to normal activity.

Moreover, the regeneration of the meniscal tissue can be also achieved by adding the patients own pleuropotent cells that are likely to differentiate into meniscal cells to the adhesive collagen-PEG hydrogel complex in situ. For example, during the arthroscopic surgery, the surgeon can remove synovial tissue or other source of fibroblasts, mince or homogenize it, and mix it with the hydrogel complex. Clot from the patient's own blood can also be used, for example, by mixing it with the adhesive collagen-PEG hydrogel to provide autologous growth factors for the stimulation of extracellular matrix production.

Additionally, the rate of polymerization of the hydrogel complex can be manipulated by controlling the pH of the buffer by addition of the weak physiologically acceptable acid or base.

D. Support Matrix

The ability to achieve the restoration of true meniscal tissue and the ability of larger gaps to heal can be enhanced by emplacement of a support matrix into the lesion or tear gap. The support matrix can be a porous Type I collagen, such as, for example, the collagen honeycomb, collagen scaffold, or collagen sponge with or without collagen-PEG hydrogel or any other hydrogel present or absorbed in the support matrix interior prior to the matrix emplacement. The support matrix is approximated to a size of the lesion or tear and deposited into the tear or lesion together with a selected hydrogel complex. Under these treatment conditions, accumulation of Type I collagen and S-GAG and fibril proliferation were determined to occur throughout the construct.

Support matrix may be any biologically acceptable and biodegradable material that provides a structural support for healing of the meniscal injury. The support matrix is prepared from such materials as Type I collagen, Type II collagen, Type IV collagen, gelatin, agarose, cell-contracted collagen containing proteoglycans, glycosaminoglycans or glycoproteins, fibronectin, laminin, bioactive peptide growth factors, cytokines, elastin, fibrin, synthetic polymeric fibers made of polyacids such as polylactic, polyglycolic or polyamino acids, polycaprolactones, polyamino acids, polypeptide gel, copolymers thereof and combinations thereof. The gel solution matrix may be a polymeric thermo-reversible gelling hydrogel.

The support matrix is preferably biocompatible, biodegradable, hydrophilic, non-reactive, has a neutral charge and be able to have or has a defined structure.

IV. Method for Treatment and Repair of Meniscal Injuries

The method of the invention is directed to treatment and repair of the meniscal injuries.

In practice, the surgeon determines a size of the meniscal tear or lesion and the extent of injury. Depending on the size of the tear or lesion, the surgeon decides if the injury will be treated just with the collagen-PEG hydrogel complex or if the support matrix needs to be deposited in conjunction with the collagen-PEG hydrogel.

In both instances, the collagen-PEG hydrogel is deposited into the tear or lesion either alone or optionally supplemented with collagenous microfibrils, synovial tissue suspension, growth hormones, growth mediators, blood components or other accelerants. For smaller size injuries, typically, the collagen-PEG hydrogel alone is deposited into the tear or lesion. For larger or complicated injuries, tears or lesions, the support matrix is deposited together with the collagen-PEG hydrogel. The collagen-PEG hydrogel may be deposited after the deposition of the support matrix or it may be introduced into the support matrix before its implantation into the tear or lesion.

In both instances, the tears or lesions are filled with the collagen-PEG hydrogel in situ during the arthroscopic surgery. Typically, the liquid collagen-PEG hydrogel gels upon contact with tissue, fills the gap completely and attaches itself to the meniscal walls surrounding the tear or lesion. There it remains until the tear or lesion closes and heals, typically within several weeks or months. Since the tear or lesion gap is filled, there is no friction between the two sides of the tear or lesion, there is no further deterioration and enlargement of the tear, nor there is an accompanying deterioration of the adjacent articular cartilage.

For this kind of treatment, the surgeon performs a simple arthroscopy during which the liquid collagen-PEG hydrogel is deposited into the tear or lesion. Then the surgeon closes the incision and the patient is instructed to resume normal activity, such as walking or exercise within several days following the surgery. Walking is very important for healing of the meniscus as it applies the intermittent hydrostatic pressure to the healing meniscal tissue. Such hydrostatic pressure has been shown to support development of a new hyaline cartilage in articular joints, as disclosed by inventors in the U.S. application Ser. Nos. 10/626,459, 10/625,822, 10/625,245, 10/882,581 and 10/104,677, issued as U.S. Pat. No. 6,949,252 on Sep. 27, 2005, all hereby incorporated by reference.

When the tears or lesions are larger, the second approach comprising deposition of the support matrix together with the collagen-PEG hydrogel is recommended. In this approach, depending on the clinical determination of the most effective treatment, the support matrix is either deposited first without having incorporated therein the collagen-PEG hydrogel, followed by deposition of the collagen-PEG hydrogel, or the support matrix incorporated with the collagen-PEG hydrogel prior to the surgery is deposited, as a complete structure, into the tear or lesion.

The current method for repair of the meniscal tears is only slightly invasive in that the arthroscopic deposition of the collagen-PEG hydrogel alone or complexed with the support matrix requires only a small incision for exact deposition of the hydrogel.

Following the surgery, the patient is encouraged to begin walking as soon as possible in order to apply the intermittent hydrostatic pressure onto deposited hydrogel. This leads to activation of the cells and their migration from the surrounding meniscal tissue into the hydrogel deposited within the tear. The attachment of the collagen-PEG hydrogel and cell migration were shown to be present, as described in the experimental studies section, upon deposition of the collagen-PEG hydrogel into the swine meniscus tear, wherein the attachment of the hydrogel to the walls of the meniscus tear and cell migration were both observed.

The current method is practical, very little invasive, safe and almost painless for the patient.

V. Experimental Studies

Experimental studies were performed to determine optimal conditions for meniscal tear treatability.

The first specific aim of the research was to determine the effectiveness of repairing tears in the avascular zone of the meniscus using collagen-PEG hydrogel with strong adhesive properties. Following activation by an accelerant, the collagen-PEG hydrogel will crosslink with the native collagen to create a strong chemical bond at the injury site. The collagen-PEG hydrogel material is, over time, remodeled and replaced with oriented fibrocartilaginous tissue.

In the first study, collagen-PEG hydrogel consisting of a polyethylene glycol (PEG)-collagen (Type I) co-polymer was be evaluated for meniscal repair. Unlike fibrin glue, collagen-PEG hydrogel co-polymers are capable of rapidly developing significant adhesive strength in situ. A crosslinking reaction between the collagen-PEG hydrogel and native collagen is initiated, providing a strong chemical bond at the interface. Currently, this type of collagen-PEG hydrogel is being utilized by inventors to fasten tissue engineered cartilage constructs in load bearing areas of the knee joint. Under these challenging loading conditions, the collagen-PEG hydrogel successfully fixes the construct in place, allowing cellular migration and tissue ingrown.

PEG based matrices have been described previously for applications such as tissue sealants, barriers to post surgical adhesion formation and vehicles for local delivery of biologically active molecules. These matrices tend to swell measurably and be highly elastic and low in tensile strength. They also degrade rapidly and resist cellular attachment.

However, the currently disclosed combination of a PEG hydrogel with type I collagen produces a unique gel with significant tensile strength and greater chemical stability than the PEG gels alone. The collagen provides additional crosslinking sites on a larger, more rigid support matrix, resulting in increased strength, decreased swelling and slower degradation in aqueous environments. In addition, the presence of collagen in the collagen-PEG hydrogel creates a highly biocompatible material which provides a suitable matrix for cell attachment, migration and proliferation.

A. Organ Culture Study

The efficacy of the collagen-PEG hydrogel for treating meniscal tears was evaluated by inventors in an organ culture study.

Figure 2:
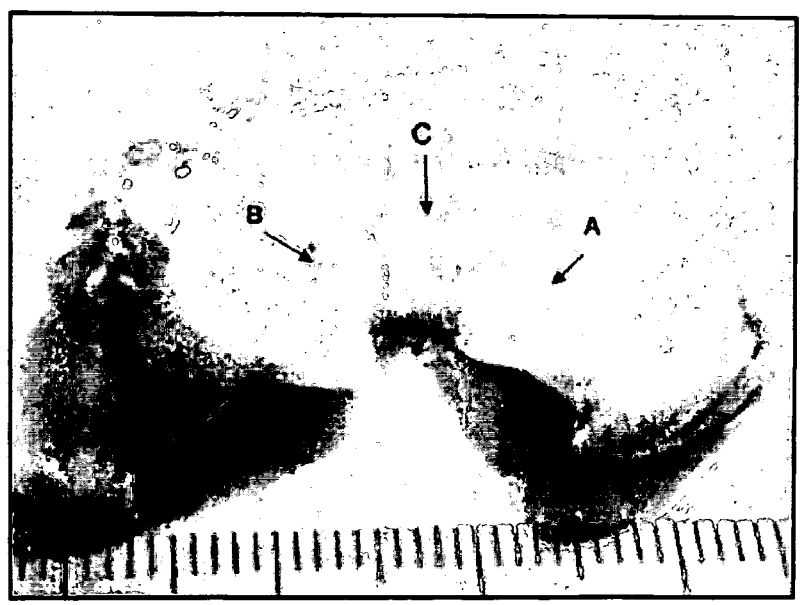
FIG. 2 is a photograph of the meniscus with tear sites indicated by A, B, and C.

The left knee from a skeletally immature swine was obtained from a local abattoir and the medial meniscus was harvested aseptically. Porcine meniscus in the organ culture is seen in FIG. 1. Three tears (A), (B) and (C), each approximately 5 mm in length, were created in the white zone of the meniscus, as seen in FIG. 2.

Three different treatments were used to repair the three tears in the meniscus. The treatments were as described in Table 1.

TABLE 1

Design of Organ Culture Study

| Group | Treatment |
|---|---|
| (A) | No treatment (control) |
| (B) | Sutures |
| (C) | Collagen-PEG hydrogel |

The tear (A) was used as a control and left without any treatment. The tear (B) was treated with sutures across the tear. The sutures are visible in FIG. 2. The tear (C) was treated with collagen-PEG hydrogel according to the invention.

After treatment, the meniscus was cultured for 2 weeks in Dulbecco's modified Eagle medium (F-12) with 10% fetal bovine serum and 1% penicillin-streptomycin. At the end of the culture period, tissue was harvested for histological evaluation. Samples were fixed with 4% paraformaldehyde and embedded in paraffin. Sections (10 μm thick) were stained with Hematoxylin and Eosin and Saffranin O.

The histological results are summarized in Table 2.

TABLE 2

Results from Organ Culture Study

| Group | Treatment | Results |
|---|---|---|
| A | No treatment (control) | No attachment, no cell integration |
| B | Sutures | No attachment, no cell integration |
| C | Collagen-PEG hydrogel | Attachment, some cell integration |

As seen in Table 2, the tear (A) shows no attachment and no cell integration. The same is observed in the tear (B) where again there is no collagen-PEG hydrogel attachment or cell integration. In the tear (C) treated with the collagen-PEG hydrogel, however, there is attachment of the hydrogel to the tissue in place where the tear was with some integration of cells also seen.

Figure 3A:
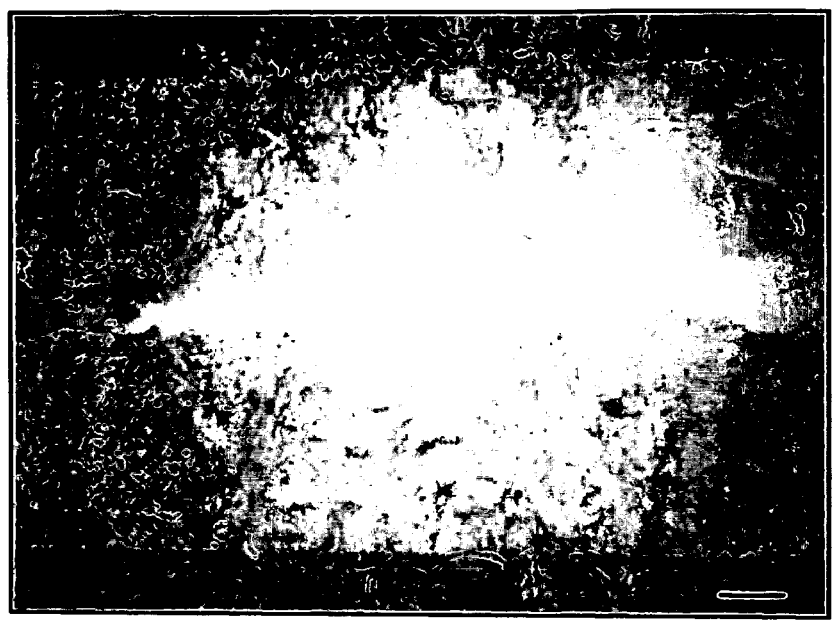
FIG. 3A is a photograph of the tear region (4×) without treatment.
Figure 3B:
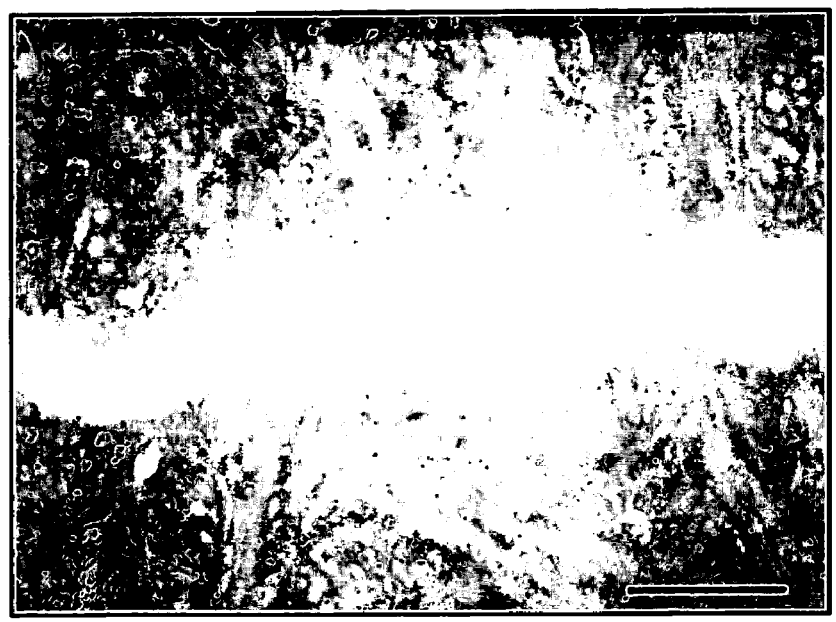
FIG. 3B is a photograph of the tear region (lox) without treatment. Scale is 250 µm.
Figure 4A:
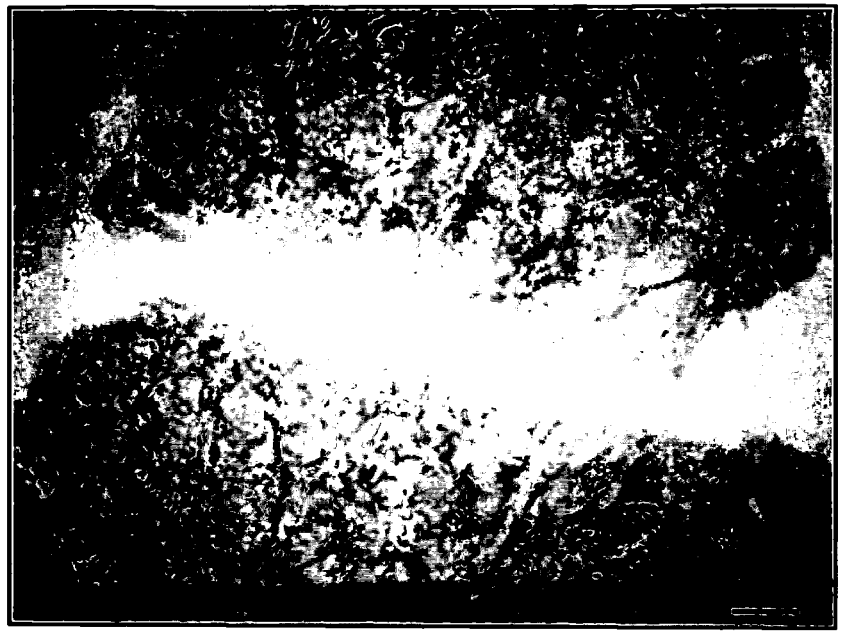
FIG. 4A is a photograph of the tear region (4×) showing a suture treatment.
Figure 4B:
FIG. 4B is a photograph of the tear region (10×) showing a site of the suture.
Figure 5A:
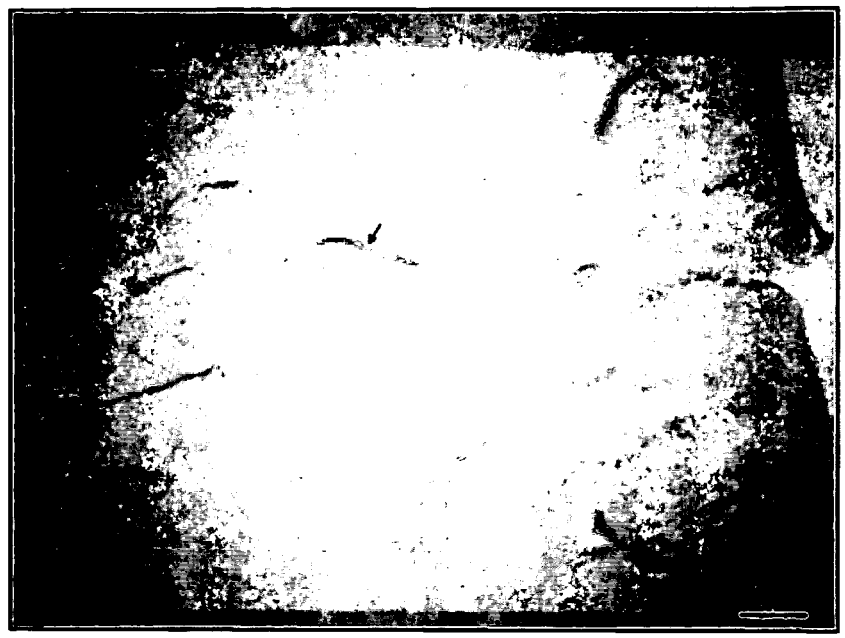
FIG. 5A shows a microphotograph of a site of the meniscus treated with collagen-PEG hydrogel (4×).
Figure 5B:
FIG. 5B is a microphotograph of a site of the meniscus treated with collagen-PEG hydrogel (10×) showing a cell integration.

Representative sections of tears (A), (B) and (C), stained with Saffranin O, are shown in FIGS. 3-5.

After two weeks in culture, the untreated control tear (A), seen in FIGS. 3A (4× magnification) and 3B (10× magnification) and the sutured tear (B), seen in FIGS. 4A (4× magnification) and 4B (10× magnification) were observed to have an open gap between the margins of the lesion, with no significant tissue formation and attachment. In contrast, the tear (C), seen in FIGS. 5A (4× magnification) and 5B (10× magnification) treated with the collagen-PEG hydrogel showed intimate contact at the interface and hydrogel filled the tear site evidencing attachment of the hydrogel to the tear.

Furthermore, some cell migration into the region of the tear occurred for the treatment group (B). This indicates that the collagen-PEG hydrogel is capable of bonding with meniscal tissue and supporting cell ingrowth into it.

B. Meniscal Healing

Castrated male Sinclair swine are utilized in the study to examine meniscal healing. Examination in the laboratory shows that the anterior region of the medial meniscus (FIG. 6) is most surgically accessible for this study. The avascular zone of the medial meniscus in this animal extends radially from the inner rim of the medial meniscus into about one third of the body of the meniscus.

Using an open surgical approach, a 5 mM full thickness longitudinal lesion is created in the anterior half of both the left and right medial menisci, approximately 2-3 mM from the inner rim. This lesion is intended to simulate the common longitudinal type tear that frequently occurs in sports-related injuries. The substantial size of the lesion results in instability of the opposing edges of the meniscal tissue, challenging the healing process further.

Lesion repair is performed immediately, according to the treatments listed in Table 3.

TABLE 3

Meniscal Healing Study Treatment Groups

| Treatment Code | Description |
|---|---|
| C1 | No treatment |
| C2 | Sutures |
| A | Collagen-PEG hydrogel and sutures |
| B | Collagen-PEG hydrogel with minced synovium |
| C | Collagen-PEG hydrogel with collagen scaffold |

There are five sites randomly assigned to each treatment group, with a total of 13 animals required for the study. In the untreated control group C1, the lesion is irrigated with sterile saline, photodocumented and the joint capsule and skin layers are closed without further intervention. The sutured control group C2 is repaired with several non-resorbing sutures evenly distributed along the length. This is followed by routine lavage, photodocumentation and closure of the surgical wound.

The collagen-PEG hydrogel is used to repair the meniscal lesion in experimental group (A). The lesion is opened with forceps and approximately 0.5 cc of the collagen-PEG hydrogel is applied to the contacting faces. The accelerator is subsequently added to activate the crosslinking reaction. The forceps are removed and the lesion is allowed to close naturally. After allowing five minutes for the adhesive to bond, several nonresorbing sutures are applied along the length of the lesion. The site is lavaged, photodocumented and closed.

Lesion repair in the (B) group is augmented with minced synovial tissue, providing a source of intra-articular fibroblastic cells. Approximately 0.5 cc of fibrous connective tissue is harvested intra-operatively from the knee joint capsule and minced aseptically. The tissue and 0.5 cc of collagen-PEG hydrogel is then mixed thoroughly. The lesion is held open with a forceps and the collagen-PEG hydrogel mixture is dispensed into the site. Following addition of the crosslinking accelerator, the forceps are removed and the collagen-PEG hydrogel is allowed to bond for five minutes. The lesion is then sutured closed using several nonresorbing sutures. The site is lavaged, photodocumented and closed.

For the (C) group, an oriented collagen sponge support matrix is placed in the lesion in an effort to guide generation of radial collagen fibers to strengthen the lesion interface. The collagen support matrix has a parallel micro-tubular structure, with the long axis of the tubules facing perpendicular to the direction of the lesion. This type of collagen support matrix has been used successfully by inventors to guide articular cartilage formation under hydrostatic pressure. The support matrix material is cut intraoperatively to fit the size of the torn area. The width of the support matrix is 0.5 mM. The tubules are coated with the collagen-PEG hydrogel prior to insertion into the lesion. Additional collagen-PEG hydrogel is applied to the margins of the lesion once the support matrix is in place. Following addition of the crosslinking accelerator, lesion is released and the collagen-PEG hydrogel is allowed to bond for five minutes. The lesion is then sutured closed using several nonresorbing sutures. The site is lavaged, photodocumented and closed.

Following post-operative recovery, the animals are allowed to move about their enclosures freely without immobilization of the operated knee joint. Any observations of stiffness, lameness, or inactivity is recorded on a daily basis, along with general observations about the overall health of the animal. At two months post-op, the animals are anesthetized and the meniscal lesions are examined arthroscopically for evidence of healing. The lesion site is gently probed with a blunt instrument to assess tissue union at the margins of the lesion. The femoral surface of the medial meniscus and the articular cartilage on the opposing femoral condyle is also visually inspected for signs of fibrillation or other degenerative changes.

At four months post-op, all animals are euthanized and the knee joints are harvested. Following careful dissection, the medial meniscus are isolated and its gross appearance is documented. The appearance of the contact regions of articular cartilage surfaces on the medial femoral condyle and medial tibia plateau is also examined and documented.

The effects of the treatments on repair of the lesion site is assessed through histological evaluation. Axial cross section slices is obtained through the lesion site and stained with hematoxylin and eosin, as well as Saffranin O, to determine the cellularity and quality of the repair tissue within the lesion. The cellular phenotype in the lesion and the region surrounding is characterized. At least three sections from each lesion is blindly scored according to a grading scheme developed from the method reported by Whatley et al. (*J. Arthroscopic Rel. Sur.*, 16(2) :127-136 (2000)) (Table 4).

TABLE 4

| | Quantitative Histological Grading Scheme | |
|---|---|---|
| Grade | Extracellular matrix organization within the lesion | Margin Contact |
| 1 | Disorganized or discontinuous fibrous tissue | <50% fill |
| 2 | Disorganized but more continuous fibrocartilage | <70% fill |
| 3 | Organized continuous fibrocartilage | 100% fill |

The grading scale is indicative of the quality of the repair tissue, with 3 being the highest quality tissue which is expected to provide the strongest, most durable lesion interface. Statistical comparisons among treated and control specimens are made using analysis of variance.

Arthroscopic evaluation of the collagen-PEG hydrogel used for treatment of meniscus according to the invention demonstrates that a collagen-PEG hydrogel has a sufficient adhesiveness for repair of the meniscal tears or lesions. This observation is confirmed by previous findings of the better surface integration with host tissue compared to controls as well as by the tests showing that the collage-PEG hydrogel has a better adhesivity than the currently commonly used tissue sealants, as seen in FIG. 8. Addition of other agents, accelerants or additives, including a synovial tissue or cells, does not affect or change the adhesiveness of a collagen-PEG hydrogel in vivo but it may assist in faster healing, particularly of the larger lesions, tears or injuries of the meniscus.

The results of the histological evaluation of meniscal or cartilage treatments in similar studies indicate that a collagen-PEG hydrogel does not cause inflammatory reactions, cytotoxicity and has no other detrimental effects on the meniscal tissue in vivo, and that collagen-PEG hydrogel is fully biodegradable and typically biodegrades in about 4 months after surgery. On the other hand, previously performed histological evaluation in untreated controls left without treatment or sutures have shown a presence of degenerative changes of the meniscal tissue as wells as formation of fibrocartilage and degradation of the meniscal extracellular matrix (ECM).

VI. Preferred Embodiments

One preferred embodiment is a method for treatment of the injured meniscus or meniscal lesions, tears or ruptures by administering to said injury, lesion, tear or rupture a collagen-PEG hydrogel.

Another preferred embodiment of the invention is a method comprising a treatment of the meniscal tissue with a collagen-PEG hydrogel supplemented with minced synovium and/or collagen scaffold. This treatment is more preferable for repair of larger lesions, tears or ruptures, as these supplements add a structural support to the collagen-PEG hydrogel in the larger voids in the meniscal tissue and assist in the reparatory and remodeling phase of the treatment.

In another embodiment of the invention, the quality of repair of the meniscal tissue is improved when the tissue is treated with collagen-PEG hydrogel supplemented with minced synovium. This embodiment might be a preferred treatment for large injuries as the synovial tissue typically may contain progenitor or stem cells and a surrounding meniscal tissue, as well as natural mechanical stimuli, such as shear stress, compression, hydrostatic pressure, or low oxygen tension, were shown to affect the cell migration and phenotypic cellular changes. All these stimuli together contribute and eventually lead to the migration of the cell into the site of injury treated with the collagen-PEG hydrogel and assist in a repair of the meniscal tissue and in its regeneration in situ.

Another preferred embodiment is a method for treatment of the injured meniscal tissue wherein said meniscal tissue is treated with a collagen-PEG hydrogel in conjunction with a collagen scaffold or another support matrix. This embodiments is particularly preferred when the injury is larger, where the hydrogel and the scaffold are better and faster integrated into the uninjured surrounding tissue than the injured tissue treated solely with collagen-PEG hydrogel. This is because the majority of the collagen in the native uninjured meniscus is type I collagen. An orientation of type I collagen fibers in the native meniscus is horizontal. Because the scaffold material is also type I collagen and because it has similar collagen orientation to that of the native meniscus, the scaffold's characteristics are able to induce cell migration from surrounding host tissue. Once cell migration into the hydrogel and scaffold occurs, natural mechanical stimuli and growth factors from surrounding native meniscus enhance and promote the meniscal tissue repair and regeneration.

Another preferred embodiment of the invention is a method for treatment of injured meniscus by providing a combined treatment comprising an administration of collagen-PEG hydrogel supplemented with minced synovial tissue deposited into the lesion or injury in conjunction with a collagen support matrix.

These and any other variation of these embodiments are intended to be within the scope of this invention.

Example 1

Lap Shear Test

This example describes a procedure and an experimental design for comparative testing of shear strength of a collagen-PEG hydrogel, fibrin tissue sealant and PEG tissue sealant.

Lap shear test was performed according to the method described in ASTM F-2255: *Standard Test Method for Strength Properties of Tissue Adhesives in Lap-Shear by Tension Loading*.

The substrates made of acrylic resin plates were prepared for attaching the porcine sausage casings used for testing. Briefly, the porcine sausage casings were soaked in water to remove the salt. The casings were opened, cut to a size 25×25 mm, and placed in the humidifier box in the incubator at 37° C. temperature. The casings were glued onto the substrate with a Gel-type cyanoacrylate adhesive Loctite QuickTite SUPER GLUE®, obtained from Henkel Consumer Adhesives, Ohio. Two control adhesives, the fibrin tissue sealant and the PEG tissue sealant, were selected. These two sealants were selected for comparison because they have a very low tissue toxicity when compared to tissue adhesives using aldehyde crosslinkers.

Five samples of each the collagen-PEG hydrogel, fibrin sealant (TISSEEL VH, Baxter, Ill.), and PEG sealant (COSEAL, Baxter, Ill.) were prepared and the two substrates were glued together with each sample. Over-lap area for each testing was 4 mm. The experimental set-up is seen in FIG. 7A and 7B. The lap shear strength of each material was evaluated by the mechanical testing machine (Model 3342, Instron, Mass.).

Comparisons were made by a one-way Student's t-test for statistical significance. Experiments were repeated three times to confirm the reproducibility of the results.

Table 5 lists the material by its product name, by its chemical composition and by the number of samples.

TABLE 5

| Material (group) | Description | Number |
|---|---|---|
| Collagen-PEG Hydrogel | Methylated type I collagen and PEG | 5 |
| TISSEEL | Fibrin sealant | 5 |
| COSEAL | PEG sealant | 5 |

Results of these comparative studies are seen in FIG. 8 and were described above.

Example 2

Single in situ Surgical Treatment for the Meniscal Repair

This example describes a protocol for 3 and 6 months preclinical studies for a single in situ surgical treatment for the meniscal repair in a swine model with a collagen-PEG hydrogel.

The study is designed to evaluate the safety and degradation period of a collagen-PEG hydrogel material in vivo, to evaluate a method for repairing meniscal tears in the avascular zone utilizing a collagen-PEG hydrogel with strong adhesiveness in vivo and to determine the necessity of the additional agents, additives or accelerants loading into a collagen-PEG hydrogel for the in situ treatment of the meniscal tears in vivo.

Animals: Miniature Hanford, Sinclair or Micro Yucatan swine

Number of animals: 8 animals

Number os menisci: 16 medial menisci

Study period: 4 months

Evaluation:

2 months post-op: arthroscopic evaluation 4 months post-op: gross anatomy, MRI, histological evaluation Table 6 is an outline of the control and experimental groups used for this study with indication of number of sites treated per one meniscus in each group.

TABLE 6

| Study Treatment Groups | | |
|---|---|---|
| Group | Description | Number of sites |
| Control 1 | No treatment | 3 |
| Control 2 | Sutures* | 3 |
| Test 1 | Collagen-PEG hydrogel with sutures* | 3-4 |
| Test 2 | Collagen-PEG hydrogel with minced synovial tissue and sutures* | 3 |
| Test 3 | Collagen-PEG hydrogel with oriented collagen scaffold and sutures* | 3 |

*Non-absorbable suture

Table 7 is an outline of the grading and evaluation of a treatment of each site on each meniscus.

TABLE 7

| Arthroscopic Evaluation | | |
|---|---|---|
| Grade | Integration with host tissue | Cartilage damage |
| 1 | No integration with host tissue | Severe damage (chondral injuries) |
| 2 | Partial integration with host tissue | Mild damage (fissures) |
| 3 | Full integration with host tissue | Non-damage (close to normal) |

Table 8 provides a quantitative histological scale for grading extracellular matrix organization within the lesion following a treatment with collage-PEG hydrogel

TABLE 8

Quantitative Histological Grading Scale

| Grade | Extracellular matrix organization within the lesion | Margin contact |
|---|---|---|
| 1 | Disorganized or discontinuous fibrous tissue | <50% fill |
| 2 | Disorganized but more continuous fibrocartilage | <70% fill |
| 3 | Organized continuous fibrocartilage | <100% fill |

Based on the previously performed studies, expected results of the arthroscopic evaluation are listed in Table 9.

TABLE 9

Expected Results of the Arthroscopic Evaluation

| Group | Description | Integration with host tissue | Cartilage damage |
|---|---|---|---|
| Control 1 | No treatment | G** 1: No integration with host tissue | G I: Severe damage (chondral injuries) |
| Control 2 | Sutures | G 1: No integration with host tissue | G 2: Mild/moderate damage (fissures) |
| Test 1 | Hydrogel with sutures | G 3: Full integration with host tissue | G 3: Non-damage (close to normal) |
| Test 2 | Hydrogel with minced synovium and sutures | G 3: Full integration with host tissue | G 3: Non-damage (close to normal) |
| Test 3 | Hydrogel with collagen scaffold and sutures | G 3: Full integration with host tissue | G 3: Non-damage (close to normal) |

**Grade

Based on the previously performed studies, expected results of the histological evaluation are listed in Table 10.

TABLE 10

Expected Results of the Quantitative Histological Grading Scale

| Group | Description | ECM organization within the lesion | Margin contact |
|---|---|---|---|
| Control 1 | No treatment | G 1: Disorganized or discontinuous fibrous tissue | G 1: <50% fill |
| Control 2 | Sutures | G 1: Disorganized but more continuous fibrocartilage | G 1: <50% fill |
| Test 1 | Hydrogel with sutures | G 2: Disorganized but more continuous fibrocartilage | G 3: <100% fill |
| Test 2 | Hydrogel with minced synovium and sutures | G 3: Organized continuous fibrocartilage | G 3: <100% fill |
| Test 3 | Hydrogel with collagen scaffold and sutures | G 3: Organized continuous fibrocartilage | G 3: <100% fill |

What is claimed is:

1. A method for in situ treatment and repair of a meniscal injury, tear or lesion, said method comprising steps:
 a) performing an arthroscopic surgical incision in a patient;
 b) determining the size and extent of the meniscal injury, tear or lesion;
 c) depositing into said meniscal injury, tear or lesion during said arthroscopic surgery an adhesive hydrogel complex consisting essentially of methylated collagen-polyethylene glycol by filling said injury, tear or lesion completely with said hydrogel complex;
 d) allowing said hydrogel complex to gel, adhere to a surrounding meniscal tissue and to bond with said surrounding tissue,
 wherein said gelled hydrogel complex bonds to the surrounding meniscal tissue and holds a torn area or lesion together during a period of healing and induces cell migration and extracellular matrix formation during such period of healing;
 e) suturing the arthroscopic incision after gelling and adhering of said hydrogel to the surrounding tissue and bonding of said collagen matrix to said surrounding meniscal tissue; and
 f) instructing the patient to begin to walk and exercise within a day or two days following the surgery.

2. The method of claim 1 wherein said meniscal injury, tear or lesion is in a white zone of the meniscus.

3. The method of claim 1 wherein the polyethylene glycol in said methylated collagen-polyethylene glycol is further derivatized with tetra-hydroxysuccinimidyl ester, tetra-thiol, or a combination thereof.

4. The method of claim 1 wherein said methylated collagen-polyethylene glycol hydrogel is supplemented with a minced synovial tissue.

5. The method of claim 1 wherein said hydrogel complex is deposited into said meniscal tear or lesion in a combination with a Type I collagen scaffold having horizontally positioned fibers.

6. The method of claim 5 wherein said hydrogel complex is further supplemented with fibroblasts, synovial tissue, autologous blot clot, a healing accelerator, a growth factor, platelet-derived growth factor (PDFG) or pleuropotent cells.

7. A method for in situ treatment and repair of a meniscal tear or lesion, said method comprising steps:
 a) performing an arthroscopic surgical incision in a patient;
 b) determining the size and extent of the meniscal injury, tear or lesion;
 c) depositing into said meniscal injury, tear or lesion during said arthroscopic surgery a porous collagen matrix and applying an adhesive hydrogel complex around said collagen matrix to affix said matrix to the site of meniscal injury, tear or lesion and to a surrounding meniscal tissue,
 wherein said adhesive hydrogel complex is consisting essentially of a methylated collagen-polyethylene glycol,
 wherein said hydrogel complex is deposited either before or after depositing said collagen matrix into said tear or lesion, and
 wherein said hydrogel complex binds said collagen matrix to a surrounding meniscal tissue;
 d) allowing said hydrogel complex to gel, adhere to a surrounding meniscal tissue and to bond with said surrounding tissue,
 wherein said gelled hydrogel complex bonded to the surrounding meniscal tissue holds a torn area or lesion together during a period of healing and induces cell migration and extracellular matrix formation during such period of healing;
 e) suturing the arthroscopic incision after gelling and adhering of said hydrogel to the surrounding tissue and bonding of said collagen matrix to said surrounding meniscal tissue; and
 f) instructing the patient to begin to walk and exercise within a day or two days following the surgery.

8. The method of claim 7 wherein said meniscal injury, tear or lesion is in a white zone of the meniscus.

9. The method of claim 8 wherein the polyethylene glycol in said methylated collagen-polyethylene glycol is further derivatized with tetra-hydroxysuccinimidyl ester, tetra-thiol, or a combination thereof.

10. The method of claim 9 wherein said support matrix is prepared from a Type I collagen, Type II collagen, Type IV collagen, collagen containing proteoglycan, collagen containing glycosaminoglycan, collagen containing glycoprotein, collagen containing fibronectin, collagen containing laminin, collagen containing a peptide growth factor, collagen containing cytokine, collagen containing elastin, collagen containing fibrin, collagen containing synthetic polymeric fiber made of polycaprolactone, polyamino acid, or polypeptide, or a combination thereof.

11. The method of claim 10 wherein said support matrix is prepared from Type I collagen as a porous collagen honeycomb, sponge or scaffold.

12. The method of claim 11 wherein said support matrix is the porous scaffold having horizontally positioned fibers.

13. The method of claim 12 wherein said hydrogel complex is further supplemented with fibroblasts, synovial tissue, autologous blot clot, a healing accelerator, a growth factor, platelet-derived growth factor (PDFG) or pleuropotent cells.

* * * * *